US005797394A

United States Patent [19]
Boyd

[11] Patent Number: 5,797,394
[45] Date of Patent: Aug. 25, 1998

[54] TRACHEAL TUBE SECURING STRAP

[75] Inventor: Michael S. Boyd, Euless, Tex.

[73] Assignee: Avail Medical Products, Inc., Dallas, Tex.

[21] Appl. No.: 794,486

[22] Filed: Feb. 4, 1997

[51] Int. Cl.$^6$ .............................. A61M 16/00; A62B 9/06
[52] U.S. Cl. ...................... 128/207.17; 128/DIG. 26; 604/179; 604/180
[58] Field of Search ................. 128/207.17, DIG. 26; 604/179, 180; 24/DIG. 11

[56] References Cited

U.S. PATENT DOCUMENTS

| | | |
|---|---|---|
| 4,378,012 | 3/1983 | Brown. |
| 4,548,200 | 10/1985 | Wapner. |
| 4,844,061 | 7/1989 | Carroll. |
| 5,038,778 | 8/1991 | Lott. |
| 5,267,967 | 12/1993 | Schneider. |
| 5,305,742 | 4/1994 | Styers et al.. |
| 5,308,339 | 5/1994 | Kalt et al.. |
| 5,357,952 | 10/1994 | Schuster et al.. |
| 5,368,024 | 11/1994 | Jones. |
| 5,411,484 | 5/1995 | Shattuck. |
| 5,490,504 | 2/1996 | Vrona et al.. |
| 5,507,285 | 4/1996 | Mota. |
| 5,546,938 | 8/1996 | McKenzie. |
| 5,702,371 | 12/1997 | Bierman ................................. 604/180 |

*Primary Examiner*—Mickey Yu
*Assistant Examiner*—Dinh X. Nguyen
*Attorney, Agent, or Firm*—Jenkens & Gilchrist

[57] ABSTRACT

A tracheal tube securing strap is adapted to wrap around a patient's head or neck and hold a tracheal tube in a desired position with respect to the patient. The securing strap includes a nonadhesive central portion that is positioned around the back of a patient's head or neck, an adhesive intermediate portion positioned on each side of the central portion which is covered by a removable release liner, and a bifurcated end portion disposed at each end of the strap and temporarily covered by separate release liners.

11 Claims, 2 Drawing Sheets

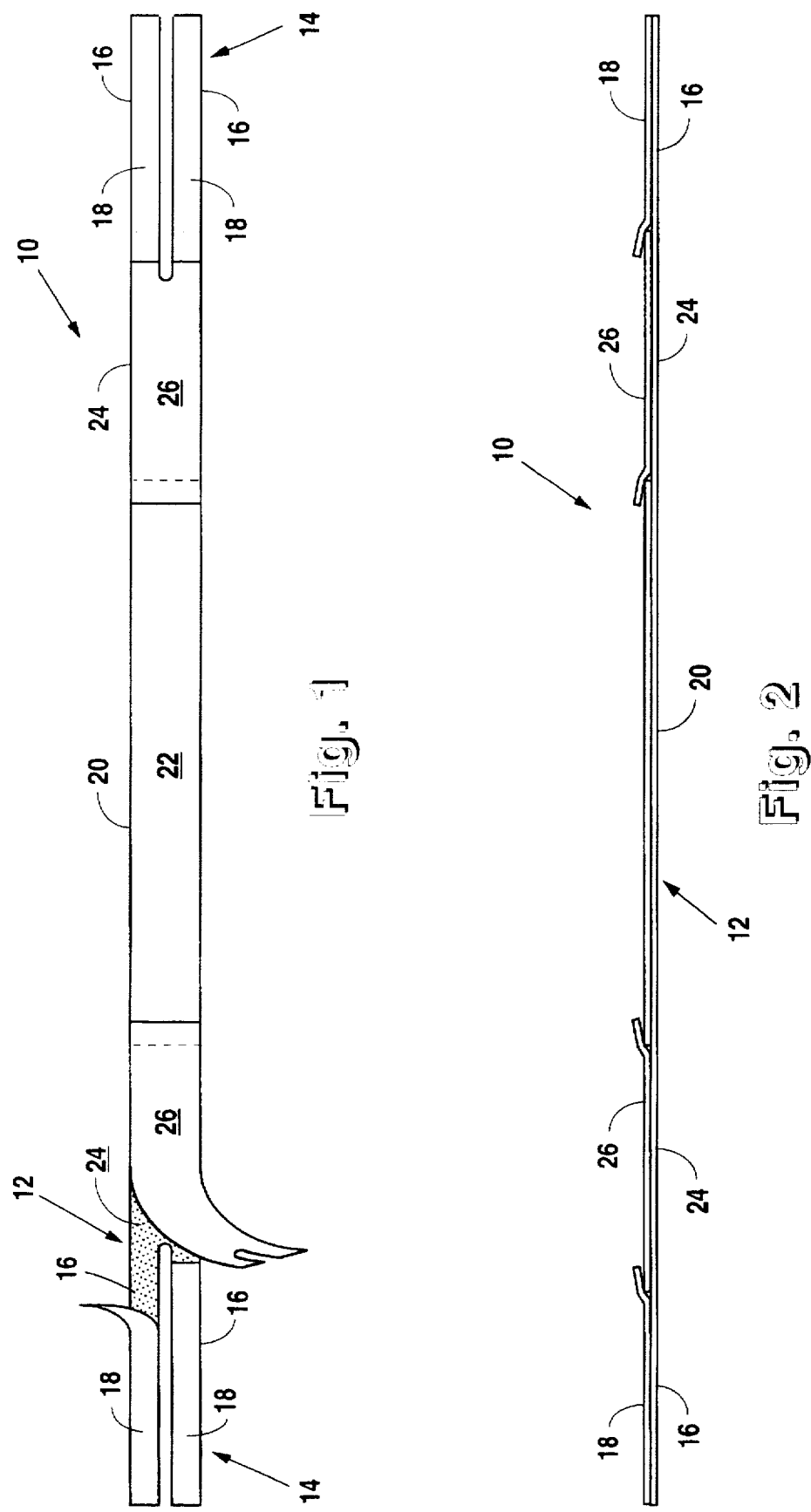

TRACHEAL TUBE SECURING STRAP

BACKGROUND OF THE INVENTION

1. Technical Field

This invention relates generally to a device for retaining a tracheal tube in a predetermined position with respect to an entry orifice in a patient, and more particularly to such device having predefined adhesive and nonadhesive portions.

2. Background Art

Tracheal tubes are commonly used to provide a passageway to the trachea of a patient. The tube may be inserted through the nose, mouth, or an opening through the neck of the patient. Once inserted, it is necessary to prevent movement of the tube with respect to the opening through which it passes. Typically, adhesive tape wrapped around the tube and extending to the adjoining skin surface of the patient, is used to secure the tube against undesired movement or dislocation. However, the use of short strips of adhesive tape to secure a tracheal tube has several inherent disadvantages. First, it is awkward to hold the tube against movement with one hand, and tear the required length of tape from a roll of tape and place the tape around the tube and secure it to the patient with the remaining hand. To overcome this problem, two people are often used to place and secure a tracheal tube; one to hold the tube in the desired position after insertion, and the other to apply the tape. Alternatively, if only one person is available, it is common practice to tear several strips, of hopefully the correct length, from a roll of tape, and temporarily stick one end of each strip on a convenient surface such as a bedside table, wall, or bed rail. This practice may result in undesirable contamination of the tape. Also, if it is desired to reposition the tube after initial placement, it is generally necessary to remove all of the previously applied tape, reposition the tube, and then apply new tape. Furthermore, it is easy for adhesive tape to stick to a patient's hair, making the tape difficult to remove and potentially painful for the patient.

The present invention is directed to overcoming the problems set forth above. It is desirable to have a means for securing a tracheal tube in a desired position that is convenient to use and will effectively prevent undesired migration of the tube once secured at a desired position. It is also desirable to have a tracheal tube securing, or retaining, means that can be partially removed to adjust or service the tracheal tube without complete removal of the securing means. Additionally, it is desirable to have such a tracheal tube securing means that is protected against sticking to a patient's hair and has adhesive surfaces that are protected against contamination until secured to a patient. Furthermore, it is desirable to have a tracheal tube securing means that is compact in size and requires minimum storage space, enabling it to be conveniently carried on an emergency medical care crash cart.

BRIEF SUMMARY OF THE INVENTION

In accordance with one aspect of the present invention, a tracheal tube securing strap includes an elongated strip having a surface coated with an adhesive material, a pair of spaced-apart ends each having a slot extending inwardly from each of the ends and forming a bifurcated end portion at each of the ends. A central portion of the elongated strip is disposed substantially midway between each of the ends. The elongated strip also has a pair of intermediate portions, with one of the intermediate portions being respectively disposed between the central portion and one of the bifurcated end portions. The tracheal tube securing strap also includes a layer of release liner removably attached to the adhesive coated surface of each member of each pair of the bifurcated end portions of the elongated strip, a layer of nonadhesive material adhesively attached to the adhesive coated surface of the central portion of the elongated strip, and a layer of release liner removably attached to the adhesive coated surface of each of the intermediate portions of the elongated strip.

Other features of the tracheal tube securing strap embodying the present invention include the elongated strip having a length to width ratio of from about 15:1 to about 25:1, and each of the pair of bifurcated end portions comprising from about 10% to about 30% of length of the strip. Other features of the tracheal tube securing strap embodying the present invention include the central portion of the elongated strip comprising from about 25% to about 35% of the length of the strip and each of the intermediate portions having a length comprising from about 5% to about 20% of the length of the strip.

BRIEF DESCRIPTION OF THE DRAWINGS

A more complete understanding of the structure and operation of the present invention may be had by reference to the following detailed description when taken in conjunction with the accompanying drawings, wherein:

FIG. 1 is a plan view of the tracheal tube securing strap embodying the present invention;

FIG. 2 is a side view of the tracheal tube securing strap embodying the present invention with overlying components of the strap shown in spaced relationship;

DETAILED DESCRIPTION OF THE INVENTION

Figure 3:
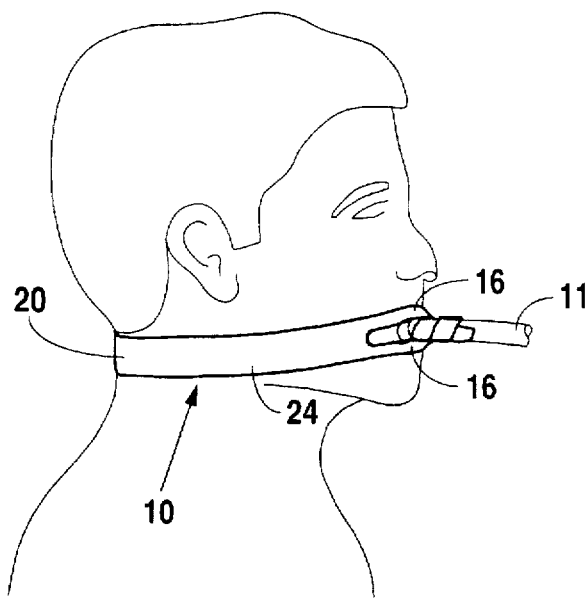
FIG. 3 is a side view of a patient with a tracheal tube extending from the patient's mouth and secured in place by the tracheal tube securing strap embodying the present invention.
Figure 4:
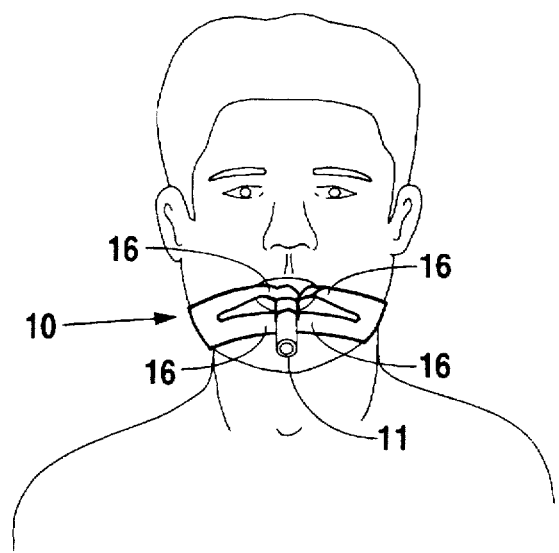
FIG. 4 is a frontal view of a patient with a tracheal tube extending from the patient's mouth and secured in place by the tracheal tube securing strap embodying the present invention.
Figure 5:
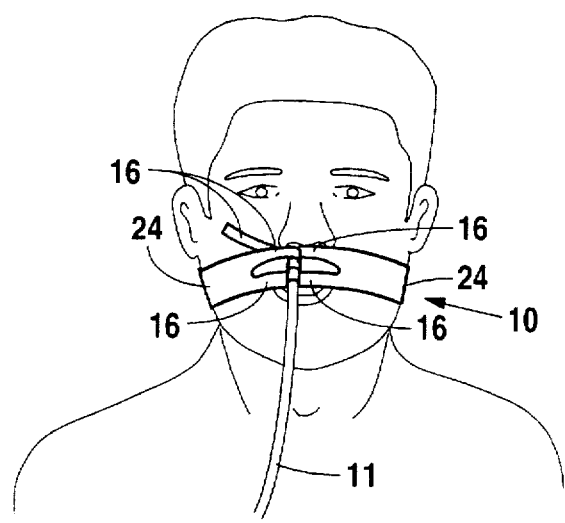
FIG. 5 is a frontal view of a patient with a tracheal tube extending from the patient's nose and secured in place by the tracheal tube securing strap embodying the present invention.

A tracheal tube securing strap 10, embodying the present invention, comprises an elongated carrier strip 12 formed of an adhesive tape having one surface coated with an adhesive material. In the preferred embodiment, the adhesive tape is preferably a cloth-backed tape that is coated with a non-allergenic adhesive. Desirably, the elongated strip 12 has a length-to-width ratio of from about 15:1 to about 25:1. In the preferred embodiment, the elongated strip 12 has an overall length of about 30 in. (76 cm) and a width of about 1.5 in. (4 cm), providing a length-to-width ratio of about 20:1. Desirably, the elongated strip 12 has a length sufficient to encircle a patient's head or neck and has adhesive portions at each end of the strip of appropriate length to secure a tracheal tube 11, as shown in FIGS. 3–5, in a desired position with respect to the patient.

The elongated strip 12 has a slot formed in each end of the strip to provide a pair of bifurcated end portions 14, one member of the pair being disposed at respective spaced apart ends of the strip 12. Each of the bifurcated end portions 14 comprises two fingers 16, each of which are covered by a layer of release liner 18 removably attached to the adhesive coated surface of the strip 12 . Desirably, each of the release liners 18 have a short tab, provided at the inward end of the liner, that is not adhesively attached to the elongated strip 12 to aid removal of the release liners 18 in a manner described below in greater detail.

Preferably, each of the bifurcated end portions 14 have a length that comprises from about 10% to about 30% of the predetermined length of the strip 12. In the preferred illustrative embodiment, each of the fingers 16 have a length of about 6.5 in. (16.5 cm), forming about 22% of the total length of the strip 12.

The elongated adhesive-coated strip 12 also includes a central portion 20 that is disposed substantially midway between each of the ends of the strip 12. The central portion 20 is covered by a layer of nonadhesive material 22, such as a disposable nonwoven material, that is adhesively secured to the adhesive-coated surface of the central portion 20. The nonadhesive layer advantageously prevents the tracheal tube securing strap 10 from sticking to a patient's hair when the strap is positioned around a patient's head or neck. Desirably, the covered central portion 20 of the elongated strip 12 has a length that comprises from about 25% to about 40% of the length of the strip 12. In the preferred illustrative embodiment, the central portion 20 of the elongated strip 12 has a length from about 8 in. (20 cm) to about 11 in. (28 cm), and preferably about 9.5 in (24 cm), extending along about 31% of the overall length of the strip 12.

The elongated adhesive strip 12 also includes a pair of intermediate portions 24, with one member of the pair being respectively disposed between the central portion 20 and a respective one of the bifurcated end portions 14 of the strip 12. Desirably, each of the intermediate portions 24 have a length comprising from about 5% to about 25% of the length of the strip 12. In the illustrative preferred embodiment, each of the intermediate portions 24 have a length of about 4 in. (10 cm), comprising about 13% of the length of the elongated strip 12. Each of the intermediate portions 24 is covered by a relatively thick layer of release liner 26 that is removably attached to the respective adhesive coated surface of the intermediate portions 24 of the elongated strip 12, and in similar manner, to the release liner 18 removably attached to each of the fingers 16, has an inwardly extending tab that is not secured to the adhesive coated surface of the strip 12. The relatively thicker release liners 26 on the intermediate portions 24, in cooperation with the layer of nonadhesive material 22 on the central portion 20, enable the securing strap 10 to be easily slipped under a reclining patient's head or neck without lifting the patient.

Thus, the adhesive surface of the intermediate portion 24 can be exposed independently of the adhesive surface in the bifurcated end portions 14 of the strip, and the tracheal tube securing strap 10 adhesively secured to the cheeks or side portions of the neck of a patient by removal of the release liners 26 prior to removing the release liners 18 from the fingers 16.

When used to retain the tracheal tube 11 at a predetermined position with respect to a patient's mouth, as shown in FIGS. 3 and 4, or nostril opening, as shown in FIG. 5, or a neck opening through the wall of the trachea, the tracheal tube securing strap 10 is positioned behind a patient's head or neck, in accordance with the desired location of the tracheal tube 11. The release liners 26 are then removed from each of the intermediate portions 24, and the securing strap 10 brought up alongside the patient's cheek or neck and adhesively attached to the cheek or neck surface. The tracheal tube 11 may then be inserted into the appropriate opening in the patient and positioned in a desired orientation. However, if desired, the tracheal tube 11 may be positioned prior to adhesively attaching the intermediate portions 24 to the patient.

The release liner 18 may then be independently removed from one of the fingers 16 and the adhesively coated finger 16 wrapped around the tracheal tube 11 and secured to the patient. The release liner 18 is then removed from a second finger 16, wrapped around the tracheal tube 11, and secured to the patient's skin. This process is repeated, as required with the remaining fingers 18, until all four fingers are desirably wrapped around the tracheal tube 11 and secured to the patient. In some applications, it may be desirable to use one one of the fingers 16 of each of the bifurcated end portions 14 to secure the tracheal tube. In those instances, one of the fingers 16 at each end of the retaining strap 10 may be attached to the patient, and the remaining strap at each end used to secure the tracheal tube 11. In other applications, one or more of the fingers 16 may not be needed, in which case the release liner 18 may remain adhesively attached to the unused fingers 16, or the unused fingers 16 removed by tearing or cutting with a knife or scissors. Advantageously, the provision of separate release liners 18, 26, with unattached tabs at the ends of each release liner, permit each respective portion of the elongated strip 12 to remain covered, and thus protected from inadvertent contamination, until ready for actual attachment to the patient's cheeks, neck, or tracheal tube.

Thus, it can be seen that the tracheal tube securing strap 10 embodying the present invention provides a number of important advantages over the conventional adhesive tape strips commonly used to position and retain tracheal tubes. The tracheal tube securing strap 10 avoids adhesive surfaces coming into contact with a patient's hair and yet is securely and independently secured to each side of the patient's face. Thus, the tube contacting fingers 16 can be partially removed from engagement with the tracheal tube 11 to shift, reposition, or otherwise service the tube 11, without removing the strap 10 from the patient. Also, the adhesive surfaces of the elongated strip 12 are protected against inadvertent contamination by the release liners 18, 26 which respectively cover the fingers 16 and intermediate portions 24 of the strip 12. Moreover, the tracheal tube securing strap 10 is easy to use, requiring only one person to secure a tracheal tube, and has a compact size, enabling the securing strap 10 to be included in the supplies normally carried on a medical emergency cart. The above advantages of the tracheal tube securing strap 10, embodying the present invention, can be readily appreciated by a health care provider, such as a doctor, nurse, or technician, particularly when working in an intensive care unit.

Although the present invention is described in terms of a preferred exemplary embodiment, with specific illustrative key dimensions and materials, those skilled in the art will recognize that changes in those illustrative dimensions and materials may be made without departing from the spirit of the invention. Such changes are intended to fall within the scope of the following claims. Other aspects, features, and advantages of the present invention may be obtained from a study of this disclosure and the drawings, along with the appended claims.

What is claimed is:

1. A tracheal tube securing strap, comprising:
    an elongated strip having a surface coated with an adhesive material continuous from one end to another, a pair of spaced apart ends each having a slot extending inwardly from each of said ends and thereby forming a bifurcated end portion at each of said ends, a central portion disposed substantially midway between each of said ends, and a pair of intermediate portions each member of said pair being respectively disposed between said central portion and a respective one of said bifurcated end portions;

a layer of release liner removably attached to the adhesive coated surface of the each member of each of said pair of bifurcated end portions of the elongated strip;

a layer of nonadhesive material adhesively attached to the adhesive coated surface of the central portion of the elongated strip; and a layer of release liner removably attached to the adhesive coated surface of each of said intermediate portions of the elongated strip;

wherein said layer of release liner of said intermediate portion is separate from said layer of release liner of said end portions and said non-adhesive material of said central portion, and said strip is configured to secure a tracheal tube around a human head.

2. A tracheal tube securing strap, as set forth in claim 1, wherein said elongated strip has a predetermined length and each of said pair of bifurcated end portions comprise from about 10% to about 30% of said predetermined length of the strip.

3. A tracheal tube securing strap, as set forth in claim 2, wherein said elongated strip has a length of about 30 in (76 cm) and each of said pair of bifurcated end portions has a length of about 6.5 in (16.5 cm).

4. A tracheal tube securing strap, as set forth in claim 1, wherein said elongated strip has a length to width ration of from about 15:1 to about 25:1.

5. A tracheal tube securing strap, as set forth in claim 4, wherein said elongated strip has a length of about 30 in (76 cm) and a width of about 1.5 in (4 cm).

6. A tracheal tube securing strap, as set forth in claim 1, wherein said elongated strip has a predetermined length and said central portion of said elongated strip comprises from about 25% to about 35% of said predetermined length of the strip.

7. A tracheal tube securing strap, as set forth in claim 1, wherein said central portion of said elongated strip has a length of from about 8 in (20 cm) to about 11 in (28 cm).

8. A tracheal tube securing strap, as set forth in claim 1, wherein said elongated strip has a predetermined length and each of said intermediate portions of the elongated strip have a length comprising from about 5% to about 20% of said predetermined length of the strip.

9. A tracheal tube securing strap, as set forth in claim 1, wherein each of said intermediate portions of the elongated strip have a length of about 4 in (10 cm).

10. A tracheal tube securing strap, as set forth in claim 1, wherein said elongated strip is formed of an adhesive coated cloth tape.

11. A tracheal tube securing strap, as set forth in claim 1, wherein said layer of nonadhesive material adhesively attached to the adhesive coated surface of the central portion of the elongated strip comprises a layer of disposable nonwoven material.

* * * * *